(12) United States Patent
Amiot et al.

(10) Patent No.: US 10,405,873 B2
(45) Date of Patent: Sep. 10, 2019

(54) COMPUTER-ASSISTED SURGERY TOOLS AND SYSTEM

(75) Inventors: Louis-Philippe Amiot, Hampstead (CA); Eric Szmutny, Philipsburg (CA); Louis Malette, St-Eustache (CA)

(73) Assignee: ORTHOSOFT ULC, Montreal (CA)

( * ) Notice: Subject to any disclaimer, the term of this patent is extended or adjusted under 35 U.S.C. 154(b) by 1918 days.

(21) Appl. No.: 11/833,451

(22) Filed: Aug. 3, 2007

(65) Prior Publication Data

US 2008/0033442 A1    Feb. 7, 2008

Related U.S. Application Data

(60) Provisional application No. 60/821,331, filed on Aug. 3, 2006.

(51) Int. Cl.
| | | |
|---|---|---|
| *A61B 17/17* | (2006.01) | |
| *A61B 5/107* | (2006.01) | |
| *A61B 5/00* | (2006.01) | |
| *A61B 34/20* | (2016.01) | |
| *A61B 34/10* | (2016.01) | |
| *A61B 90/11* | (2016.01) | |

(52) U.S. Cl.
CPC .......... *A61B 17/175* (2013.01); *A61B 5/1077* (2013.01); *A61B 5/4528* (2013.01); *A61B 17/1746* (2013.01); *A61B 34/20* (2016.02); *A61B 5/4504* (2013.01); *A61B 90/11* (2016.02); *A61B 2034/102* (2016.02); *A61B 2034/105* (2016.02); *A61B 2034/108* (2016.02); *A61B 2034/2055* (2016.02); *A61B 2034/2065* (2016.02); *A61B 2562/02* (2013.01); *A61B 2562/046* (2013.01)

(58) Field of Classification Search
CPC .............. A61B 17/1742; A61B 17/175; A61B 2017/1778; A61B 17/16; A61B 17/1615; A61B 17/17; A61B 17/1739; A61B 17/1746; A61B 17/1753
USPC ......... 606/86 R, 87, 89, 96–97, 104, 79, 80; 600/587, 594–595
See application file for complete search history.

(56) References Cited

U.S. PATENT DOCUMENTS 2,416,228 A * 2/1947 Sheppard ...................... 408/105
4,524,959 A * 6/1985 Kubo ............................ 269/43
(Continued)

FOREIGN PATENT DOCUMENTS

JP           2003279306      10/2003
WO     WO-2004/030559       4/2004
(Continued)

OTHER PUBLICATIONS

U.S. Appl. No. 60/691,164, filed Jun. 2005, Hodgson et al.

*Primary Examiner* — Si Ming Ku
(74) *Attorney, Agent, or Firm* — Norton Rose Fulbright Canada LLP

(57) ABSTRACT

A surface digitizing tool has a film of micro-sensor elements, with each micro-sensor element related in a network affected by a shape of the film. The film is flexible to conform to a shape of a selected surface of an object. A processing unit receives signals from the micro-sensor elements of the network. The processing unit has a model generator producing a model of the selected surface of the object from the signals of the network of resistive elements. A positioning frame aligns a position and orientation of a drilling tool with respect to a bone element.

6 Claims, 7 Drawing Sheets

(56) References Cited

U.S. PATENT DOCUMENTS

| | | | |
|---|---|---|---|
| 4,896,663 A * | 1/1990 | Vandewalls | A61B 17/175 269/236 |
| 5,752,962 A * | 5/1998 | D'Urso | A61B 90/11 128/857 |
| 5,817,098 A | 10/1998 | Albrektsson et al. | |
| 6,127,672 A * | 10/2000 | Danisch | 250/227.14 |
| 6,989,015 B2 * | 1/2006 | Daum | A61B 90/11 606/130 |
| 6,996,487 B2 | 2/2006 | Jutras et al. | |
| 7,794,469 B2 * | 9/2010 | Kao | A61B 90/11 606/130 |
| 2002/0193801 A1 * | 12/2002 | Marchione et al. | 606/96 |
| 2003/0204150 A1 * | 10/2003 | Brunner | 600/590 |
| 2005/0010230 A1 * | 1/2005 | Crofford | A61B 17/175 606/81 |
| 2005/0113841 A1 * | 5/2005 | Sheldon et al. | 606/88 |
| 2006/0271058 A1 * | 11/2006 | Ashton et al. | 606/96 |
| 2008/0183179 A1 * | 7/2008 | Siebel et al. | 606/89 |

FOREIGN PATENT DOCUMENTS

| | | | |
|---|---|---|---|
| WO | WO-2005/027755 | 3/2005 | |
| WO | WO 2005082258 A1 * | 9/2005 | A61B 17/17 |
| WO | WO-2005/102202 | 11/2005 | |
| WO | WO-2006/095109 | 9/2006 | |

\* cited by examiner

COMPUTER-ASSISTED SURGERY TOOLS AND SYSTEM

CROSS-REFERENCE TO RELATED APPLICATION

This patent application claims priority on U.S. Provisional Patent Application No. 60/821,331, filed on Aug. 3, 2006. This patent application incorporates by reference U.S. patent application Ser. No. 11/339,499, by the present assignee, published as United States Publication No. 2006/0189864.

FIELD OF THE APPLICATION

The present application generally relates to Computer Assisted Surgery (CAS) such as hip joint resurfacing surgery and, more precisely, to a method for assisting hip joint resurfacing surgery and like orthopaedic surgery with CAS systems.

BACKGROUND OF THE APPLICATION

Orthopaedic surgery is constantly evolving to lessen the effects of surgery on patients. In order to reduce the amount of post-surgical pain, new methods and tools have been developed in CAS to minimize the invasiveness of surgery. Moreover, CAS systems constantly involve new features to accelerate surgeries.

Also, CAS is more commonly used in surgical rooms, so as to provide precision and accuracy to the surgeon. By way of CAS, position and orientation information is gathered during the surgical procedures, so as to provide to the surgeon real-time visual/digital data about bone alterations, tool navigation, and surgical parameters.

One of the issues pertaining to the efficiency of CAS is the creation of frames of references and the digitization of bone models. In such cases, a plurality of points are digitized on the bone elements intraoperatively, which represents a time-consuming operation.

Hip joint resurfacing surgery involves the introduction of hip joint components in a patient. The acetabulum and the femoral head are resurfaced so as to receive an acetabular cup implant and a femoral head implant, respectively. The femoral head implant consists of a ball head received at an end of the resurfaced femoral head. Therefore, the implanted femoral head and the cup (i.e., acetabular or pelvic implant) coact to create the artificial hip joint. In comparison with total hip joint implanting surgery, the hip joint resurfacing surgery removes a relatively small amount of bone while preserving joint stability.

Different output values are of concern in hip replacement surgery. In order to reproduce a natural and/or improved gait and range of motion to a patient, the position and orientation of the implants, the offset of the femur and the limb length must be considered during surgery. The work of the surgeon during hip replacement surgery will have a direct effect on these output values.

Known hip joint resurfacing surgery techniques presently involve specific tools so as to obtain precise position and orientation for the implants. As various types of reamers are used to resurface the femoral head, a plurality of alignment steps are performed to align the tools with the cuts to be made. It is, for instance, of nonnegligible importance that the femoral neck not be damaged (i.e., notched) by the reamers, to prevent fracture-prone weaknesses in the femoral head. Moreover, the resurfacing must be as precise as possible, for instance, to reduce the amount of cement required for implanting the ball head implant to the resurfaced ball head.

SUMMARY OF THE INVENTION

It is an aim of the present invention to provide a novel tool and system for digitizing bone surfaces in computer-assisted surgery.

It is a further aim of the present invention to provide a novel positioning frame for adjusting a position and orientation of bone-altering tools in computer-assisted surgery.

Therefore, in accordance with the present invention, there is provided a model generator system for generating models of objects, comprising: a surface digitizing tool having a film of micro-sensor elements, with each micro-sensor element related in a network affected by a shape of the film, the film being flexible to conform to a shape of a selected surface of an object; a processing unit for receiving signals from the micro-sensor elements of the network, the processing unit having a model generator producing a model of the selected surface of the object from the signals of the network of resistive elements.

Further in accordance with the present invention, there is provided a positioning frame for aligning a position and orientation of a drilling tool with respect to a bone element, comprising: a connector portion adapted to releasably grasp the bone element; a support portion operatively connected to the connector portion and positioned with respect to a portion of the bone element to be drilled; an alignment tube operatively connected to the support portion, the alignment tube being adapted to receive a working end of a drill to align the drill with the bone element; and joints between the alignment tube and the connector portion to adjust a position and an orientation of the alignment tube with respect to the bone element.

Still further in accordance with the present invention, there is provided a method for drilling a bone element in computer-assisted surgery, comprising: providing a positioning frame having a drill guide with adjustable degrees of freedom for the drill guide in the positioning frame, and a computer-assisted surgery system providing orientation data associated with tracking of the drill guide and of a frame of reference of the bone element; clamping the positioning frame to the bone element such that the drill guide is in the vicinity of a portion of the bone element to be drilled; displacing the drill guide along the degrees of freedom as a function of the orientation data from the computer-assisted surgery, until a desired orientation is reached for the drill guide; and drilling the bone element by passing a drill bit through the drill guide in the desired orientation.

Still further in accordance with the present invention, there is provided a method for generating a model of an object comprising: providing a film of micro-sensor elements, with an individual position in the film of each said micro-sensor element known; obtaining a signal from each said micro-sensor element when the film is shaped to model an object; determining a shape variation of the film at each said micro-sensor element from the signal; and generating a model of the object from the shape variation and the individual position of each said micro-sensor element.

DESCRIPTION OF THE PREFERRED EMBODIMENT

Figure 1:
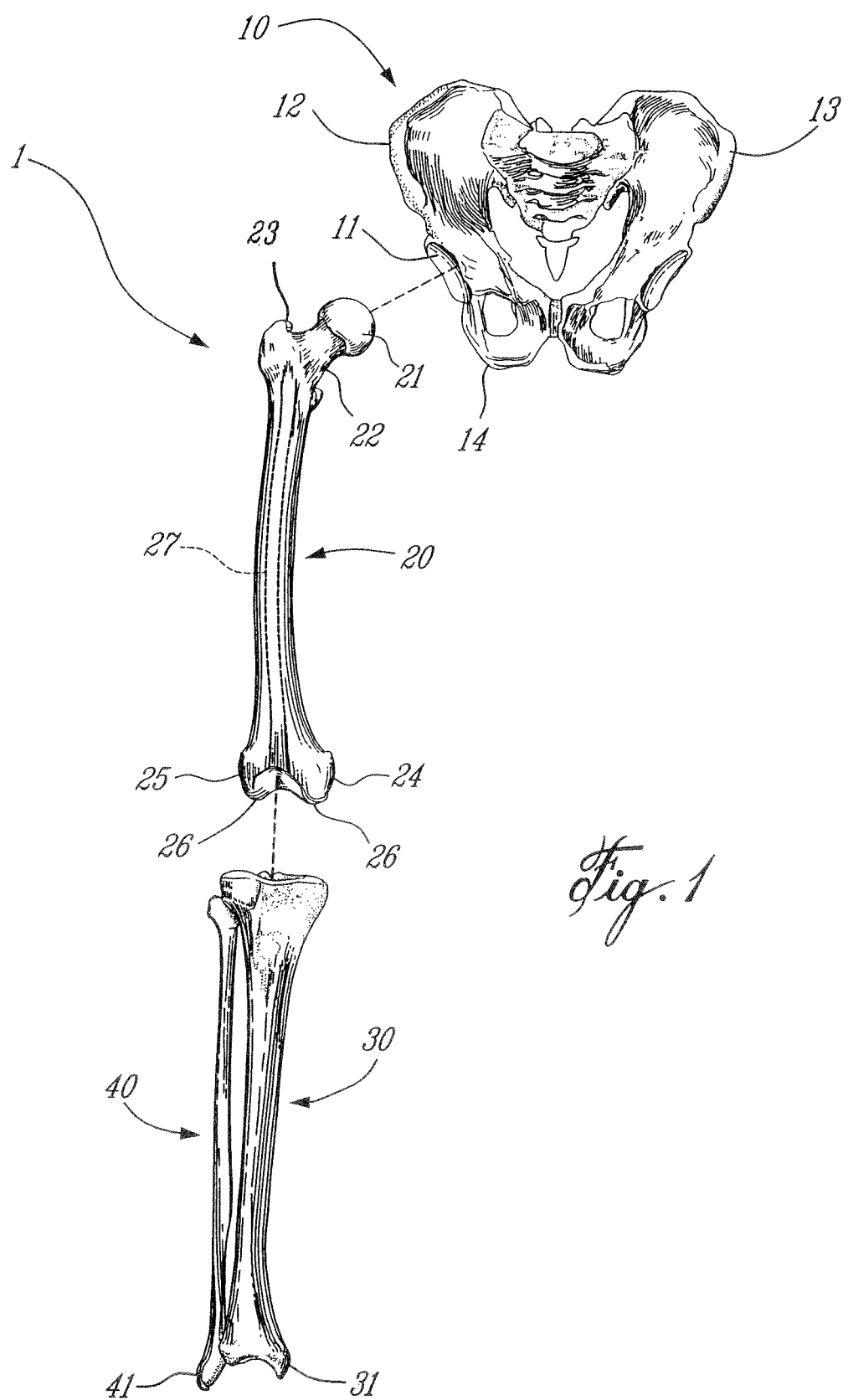
FIG. 1 is a front elevation view of leg bones involved in a hip replacement method.

According to the drawings, and more particularly to FIG. 1, bones of the leg that will be involved in the hip replacement surgery of the present embodiment are generally shown at 1. FIG. 1 is provided as reference for the description of the steps of the hip replacement surgery method described herein. The bones are the pelvis 10, the femur 20, the tibia 30 and the fibula 40. Hereinafter, parts of these bones will each be referenced by numerals from the same numeric decade. For instance, parts of the pelvis (e.g., the acetabulum 11) will bear reference numerals between 11 and 14.

Figure 2:
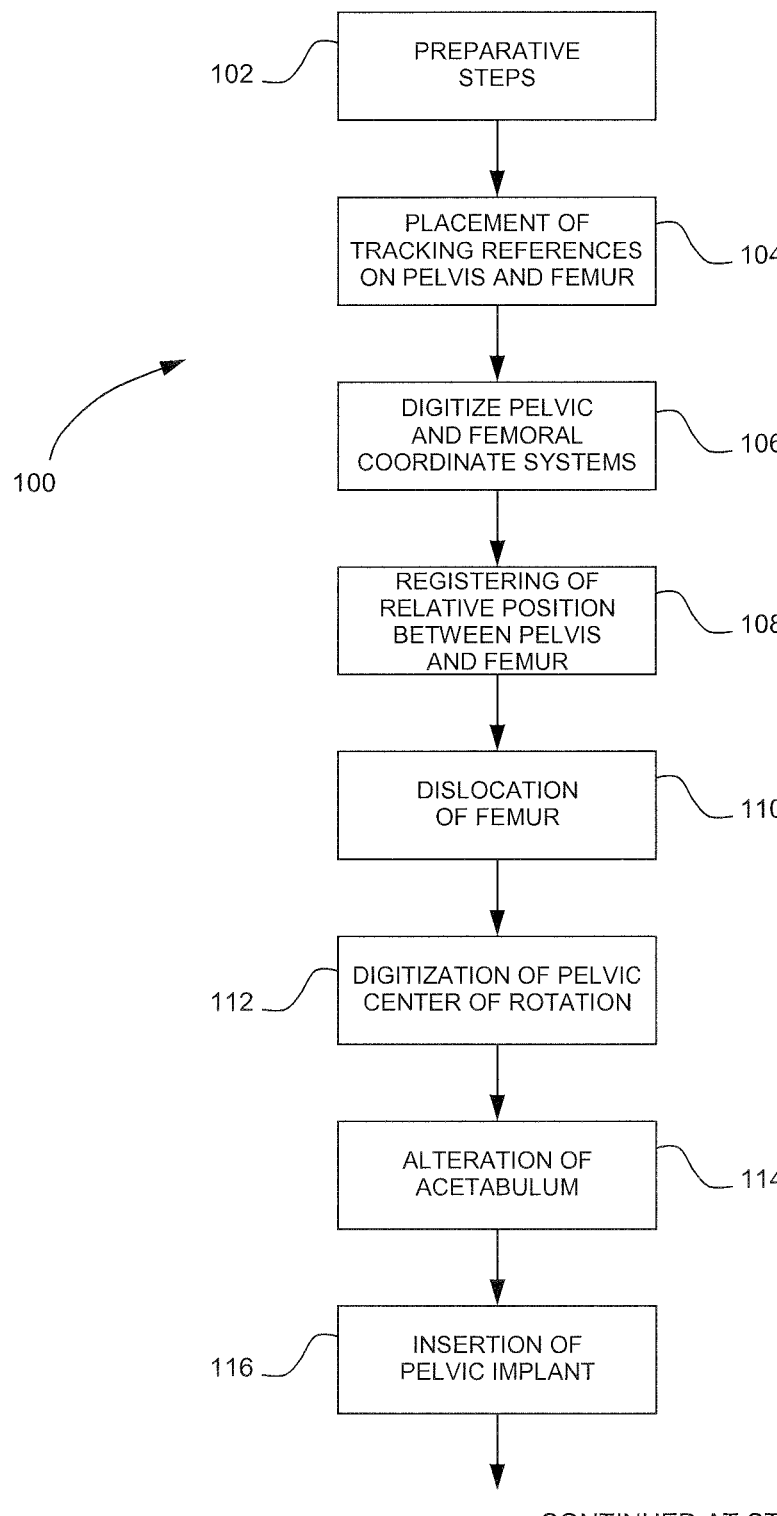
FIG. 2 is a flowchart of a method for hip joint resurfacing surgery.
Figure 2:
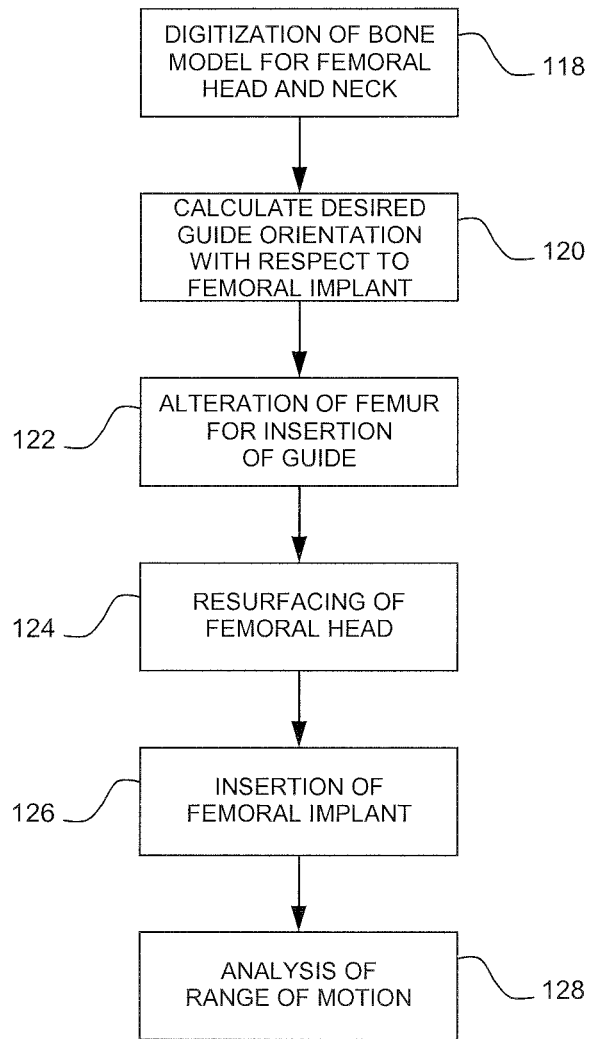

Referring to FIG. 2, a method for hip joint resurfacing surgery in accordance with the present embodiment is generally shown at 100. Although the method 100 is referred to in the singular, various choices of procedure will be given to the surgeon, as will be set forth in the forthcoming description, according to the preferences of the surgeon. A plurality of sequences can be derived from the method 100 according to the decisions of the surgeon.

In Step 102, preparative steps for surgery are effected. Namely, general patient information can be entered into a CAS system for opening a patient file. For instance, a general patient profile can be entered, consisting of the name, birth date, identification number, sex and the like, the side to be operated, as well as more specific data pertaining to the surgery, such as leg length discrepancy (with the identification of the longer leg), if applicable, and parameters to define the flow of the application and the display. For instance, the leg length discrepancy is measured using X-rays of the hip joint. More precisely, the leg length discrepancy is measured from the vertical comparison between the lesser trochanters. These X-rays are typically taken during the diagnostic stages leading to surgery, so they are usually available for hip joint surgery. Alternatively, X-rays may be taken as part of Step 102. It is also contemplated to import DICOM files or digital X-rays.

It is pointed out that the general patient information can be entered preoperatively. Moreover, the entering of the general patient information is straightforward such that the surgeon need not be involved. However, in order to minimize the preoperative procedures, actions of Step 102 can be performed at the beginning of the surgical session, during the short time span preceding the surgery.

Other values that will potentially be considered in the method 100 are inclination and anteversion for the pelvic implant, CCD (collodiaphyseal angle) and anteversion for the femoral implant.

The calibration of the various surgical tools to be used is done. For instance, a calibration base and method, as set forth in U.S. Pat. No. 6,996,487 by Jutras et al., can be used for the calibration. Also, correspondence between the tracking of the tools and the display on a CAS system can be verified in further calibration steps included in Step 102. A permanent calibration system can also be used, as set forth in International Publication No. WO 2005/102202.

Surgery is initiated between Step 102 and subsequent Step 104, by the surgeon exposing the hip joint. No computer assistance is required thereat.

In Step 104, the trackable references are secured to the pelvis with a pelvic modular reference, and to the femur with a femoral modular reference. The pelvic modular reference can be inserted in a cranial or lateral position. Alternatively, the trackable references may be secured prior to exposing the hip joint.

It is pointed out that the pelvic modular reference, in a preferred embodiment, is positioned while the patient is in supine decubitus. Moreover, as will be described hereinafter, the pelvic coordinate system and table reference must also be digitized in supine decubitus. After those manipulations, the patient can be repositioned in lateral decubitus.

The femoral modular reference can be inserted at the proximal third from the femoral head of the femur or at the distal third from the femoral head. These insertion points are examples, as any other suitable point on the femur is considered. Positions of the trackable references are, for example, (1) looking posterior and towards the head, prior to dislocation, and (2) a longer trackable reference, looking posterior, for the dislocated position. It is contemplated to use a single modular base.

In Step 106, it is contemplated to digitize the coordinate system in lateral decubitus. It is also contemplated to collect posture information, as described in International Publication No. WO 2004/030559 A1, by Jansen et al. Criteria may be used to validate the points taken and the computed surface.

In Step 106, a pelvic coordinate system and a femoral coordinate system are digitized. In an embodiment, the pelvic coordinate system is digitized with a registration pointer. In an embodiment, three points are taken on the pelvis 10 to create the frontal plane of the acetabular coordinate system. Referring to FIG. 1, there is one point on the iliac crest 12 of the operated side, one point on the contra lateral iliac crest 13, and one point on one of the two pubic tubercles 14 of the pelvis 10. To be generally aligned, the points digitized on the iliac crests 12 and 13 are taken at the outermost anterior point of the iliac crests 12 and 13. The points digitized on the iliac crests 12 and 13 are preferably taken directly on the soft tissue covering the bone pelvis on the iliac crests, as the soft tissue is relatively thin thereon. The point on the pubic tubercle 14 completes a first plane, the frontal plane. A second plane, the transverse plane, is perpendicular to the frontal plane and includes the points on the iliac crests. A third plane, the sagittal plane, is perpendicular to the frontal and transverse planes.

Supplemental information regarding the frontal plane can be obtained for various postures of a patient. For instance, trackable references can be used to gather information about sitting, standing and walking postures. This information can be used to adjust the orientation of the frontal plane, as these postures can provide information not available from the typical lying posture in which a patient is during surgery. This information can influence the anteversion positioning of the implants.

It is possible to obtain anteversion and/or inclination values of the acetabulum of the patient, to be used as a reference (e.g., comparison basis) later in the surgery. To do so, points are digitized using a registration pointer on the generally circular edge of the acetabulum 11 and a plane is defined from these points. A normal to this plane and the pelvic frontal plane give the anteversion angle. The normal to this plane is projected onto the acetabular frontal plane to give an inclination angle with a cranial-caudal axis.

For the digitization of the femoral coordinate system, it is contemplated to collect five points of reference on the leg to the CAS system, which is equipped with software that will create the femoral coordinate system.

Referring to FIG. 1, a first point is taken on the tip of the greater trochanter 23 of the femur 20, and will be defined as a starting point of an anatomical axis of the femur 20. Thereafter, points are taken on the medial and lateral epicondyles 24 and 25 of the femur 20, respectively. A midpoint between the medial epicondyle and lateral epicondyle points, in alignment therewith, is defined as an endpoint of the anatomical axis of the femur. The fourth and fifth points are taken on the medial malleolus 31 of the tibia 30 and on the lateral malleolus 41 of the fibula 40, with the leg being bent at the knee. By having the leg bent at the knee, the tibia 30 stands on the posterior condyles 26 of the femur 20. Therefore, an assumption is made wherein an aligned midpoint of the medial and lateral malleoli points is said to define a plane (i.e., sagittal plane) with the anatomical axis, with an axis of the knee being normal to the sagittal plane. The frontal plane is perpendicular to the sagittal plane, with the anatomical axis lying therein. The transverse plane is perpendicular to the sagittal and frontal planes, and can be positioned at any height. With the anatomical axis and the midpoint of the malleolus region digitized, the femoral coordinate system, i.e., the femoral frame of reference, is complete. It is noted that it is not required to measure two points to obtain a midpoint of the malleolus region. As this latter point will be in the sagittal plane, the only requirement is that a point is taken at a midpoint of the malleolus region, and may thus be placed approximately by the operator.

It is pointed out that the projection values described herein (e.g., inclination, anteversion, etc.) are based on the acetabular and the femoral coordinate systems. As it is contemplated to use alternative methods of digitizing the acetabular and the femoral coordinate systems, in addition to the preferred methods of Step 116, the projection values would be related to the alternative acetabular and femoral coordinate system. For instance, another contemplated method for creating coordinate systems is described in U.S. Patent Application No. 60/691,164, to Hodgson et al.

Other methods to gather information pertaining to surgical parameters are as follows. (1) The user digitizes a point on the greater trochanter before dislocation and retakes the same point, with the leg aligned in the same orientation, after reduction. (2) The user digitizes a point on the greater trochanter before dislocation and the system helps the user to replace the leg in the same orientation after reduction. The leg length and the offset are automatically computed when the leg is positioned in range of the initial position before dislocation. (3) The user digitizes many points near the greater trochanter before dislocation, the center of rotation of the acetabulum as described in Step 112 and the same points after reduction. The system aligns these points and computes the leg length and the offset. Also, in each case, the CAS system may help the operator in placing the leg in a required initial position.

In optional Step 108, a relative position between the pelvis and the femur is registered with respect to the trackable references. The leg is simply left in a straight position, to align with a longitudinal axis of the body, and a relative position is acquired between tracking references secured to their respective bones.

In Step 110, the femur is dislocated from the pelvis, so as to expose the acetabulum 11 and the femoral head 21 and neck 22.

Figure 3:
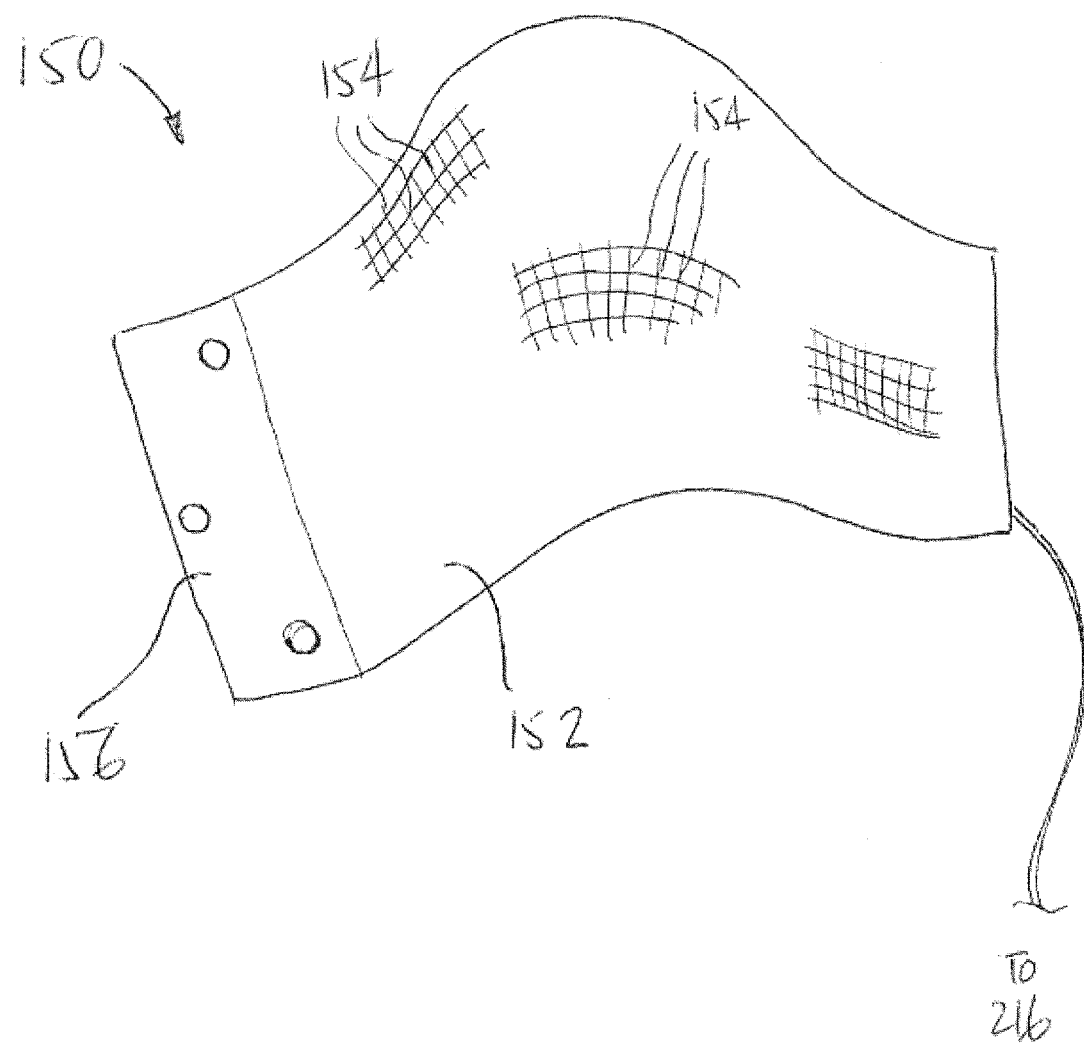
FIG. 3 is a schematic view of a surface digitizing tool in accordance with a preferred embodiment of the present invention.

In Step 112, a center of rotation is digitized for the acetabulum, by taking reference points on the surface of the acetabulum 11. Referring to FIG. 3, a surface digitizing tool used to digitize the reference points on the surface of the acetabulum is generally shown at 150.

The surface digitizing tool 150 has a flexible film 152. The flexible film 152 is made of a grid forming a network of micro-sensor nodes 154. More specifically, the micro-sensor nodes are nodes changing characteristics as a function of the shape of the flexible film 152. Accordingly, the overall shape of the flexible film 152 is calculable by determining the interrelations between adjacent nodes 154.

Various configurations are considered for the flexible film 152. According to one embodiment, the flexible film 152 is formed of a series of micro-pipes aligned to form a grid support by a substrate such as a textile or plastic film. Each micro-pipe contains an electrolyte (e.g., NaCl, or like biocompatible electrolytes), varying in electrical characteristics (e.g., resistivity, capacity) as a function of pressure sustained by the micro-pipe (e.g., torsion resulting from the deformation of the grid to match a surface). Each micro-pipe is divided in a plurality of micro-pipe sections wired to allow the detection of any variation in the electrical characteristics of the micro-pipe sections as a result of shape variations. As the position of each micro-pipe section is known, it is then possible to generate a 3D model from the calculated shape variations.

In the micro-pipe embodiment, the size and spacing between micro-pipes are selected as a function of the resolution required for the 3D model of the object. As an example, spacing ranging between 0.5 to 1.0 mm between adjacent micro-pipes is sufficient to obtain a suitable resolution for a femoral head of a diameter of 60 mm, in the event that the flexible film 152 is used in hip replacement or resurfacing surgery.

In another embodiment, the film is formed fs strands made of a substrate having variable characteristics when curved or bent. As an example, quartz crystal is a suitable substrate as its electrical characteristics vary when subjected to pressure. Accordingly, it is considered to provide the flexible film 152 made of quartz crystal substrate with a mesh of electrical wires capturing the electrical characteristics, and variations thereof, for different sections along the strand.

In another embodiment, the flexible film 152 is a metallic film associated with a mesh of electrical wires capturing the variations in electrical characteristics at predetermined locations on the metallic film.

Figure 6:
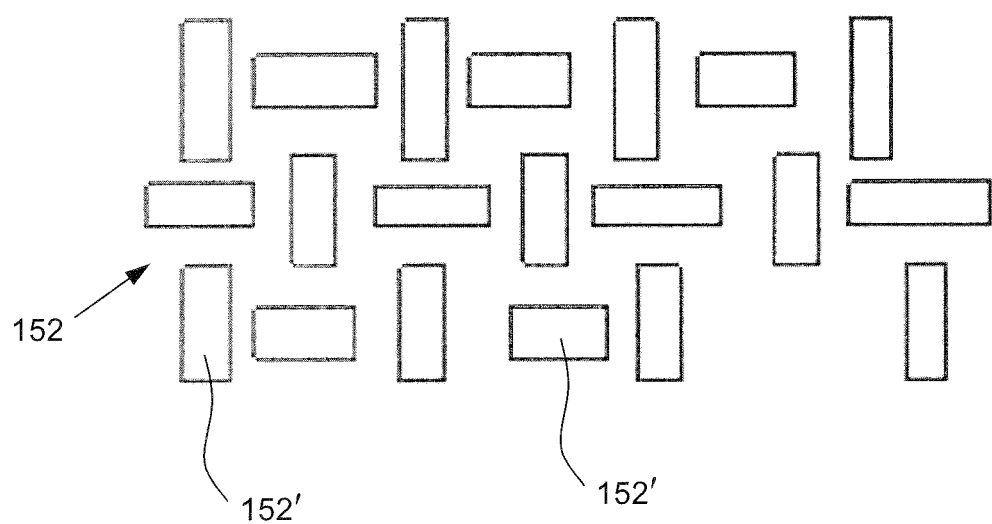
FIG. 6 is a schematic view of a pattern of micro-elements as used in one embodiment of a flexible film of the surface digitizing tool of FIG. 3.

In another embodiment, the flexible film 152 has a mosaic of micro-elements arranged in a predetermined pattern, an example of which is generally shown in FIG. 6, with micro-elements being illustrated by 152' having rectangular shapes (amongst other considered shapes), with the micro-elements aligned in a quasi-uniform pattern (single or multiple layers), and sandwiched between charged plates. Each micro-element 152' has a positive end and a negative end, with the polarity being proportional to the pressure sustained by the flexible film as a function of its deformation. Scans are performed in both directions of alignment, whereby a 3D model can be digitized from the result of both scans.

In another embodiment, the flexible film 152 is a mesh of optical fibers, with Braggs gratings distributed along each optical fiber. The light captured at the exit of the optical fibers provides information on the deformation of the flexible film 152. A 3D model can be created by associating the positions of the Braggs gratings in the optical fibers to the deformation information obtained from the captured light.

In order to determine the position of each node, the flexible film 152 is connected to a model generator, as will be described in further detail hereinafter, which will calculate the 3-dimension shape of the flexible film 152 by determining the position of each node 154, to form a mesh of points.

In order to calibrate and relate the 3-dimensional model obtained from the flexible film 152 to a coordinate system, a trackable reference 156 is secured to the flexible film 152 in a known relation. In the example of FIG. 3, the trackable reference 156, a passive trackable reference, is a known optical pattern, so as to be tracked for position and orientation by a CAS system. Therefore, a resurfacing processing unit calculates the position and orientation of the 3-dimensional model with respect to the frames of reference by relating the points of the nodes 154 to the trackable reference 156.

As an alternative to the trackable reference 156, it is contemplated to provide an active tracker connected to the flexible film 152. For example, magnetic (e.g., electromagnetic), infrared and RF emitters are considered for use as reference 156, provided the use of such technologies is acceptable in emergency-room environments.

In order to have the flexible film 152 take the shape of the acetabulum, it is contemplated to cover a generally spherical resilient member with the flexible film 152. The combination of the flexible film 152 and resilient member is then fitted into the acetabulum, at which point the resilient member exerts an outward pressure forcing the flexible film 152 to take the shape of the acetabulum.

The use of the surface digitizing tool 150 is advantageous in that the positions of points are gathered in one step, and therefore represent an economy of time. Moreover, as points are currently digitized one by one using a pointer, the risk of handling error is increased. The resolution of the flexible film 152 is typically controlled and tested during its manufacturing. The flexible film 152 is either disposable or sterilizable for further uses. The surface digitizing tool 150 is not limited to being used in resurfacing surgery, but may be used in a plurality of surgical procedures in which it is desired to digitize bone models. Moreover, it is also considered to use the surface digitizing tool 150 along with a processing unit to generate digital models of objects other than anatomical parts. In many cases, the digital model does not need to be related to a position and orientation, whereby the surface digitizing tool 150 is not necessarily provided with the trackable reference 156.

A center calculator (e.g., sphere fitter algorithm) is used to find the acetabular center of rotation from the 3-dimension shape obtained, and will be described hereinafter with the description of a hip resurfacing CAS system. The acetabular center of rotation is therefore known as a function of the tracking reference on the pelvis 10. In order to ensure precise results, it may be required that a predefined number of points be taken until validation criteria are met. Visual validation of the sphere found by the algorithm can also be performed. The center of rotation and the diameter found may be displayed. Points are digitized in the fossa (depth of the acetabulum). If the center of rotation of the acetabulum is known, it is not necessary to digitize the center of rotation of the femoral head. However, it can be done without departing from the spirit of the present embodiment.

In Step 114, the acetabulum is altered in view of accommodating the acetabular cup implant. In order to guide the operator in altering the acetabulum, reamer position and orientation information is preferably provided, such that an axis of actuation of the reamer is for instance visually displayed. The previous acetabular center of rotation is known as a function of the tracking reference secured to the pelvis 10, as it was acquired in previous Step 112. Preferably, the reamer is tracked for position and orientation.

Examples of information that can be provided to the operator are as follows: generic 2D images, mosaic or mesh in 3D viewers along with drive shaft/reamer assembly in real time and/or display targeting views to help the user to align with target values, frontal and lateral views, inclination, inclination adjusted with the pelvic tilt, anteversion, anteversion adjusted with the pelvic tilt angles in real time, 3D position of the reamer center of rotation relatively to the acetabulum center of rotation, the distance between the reamer pole and acetabular wall.

The diameter of the pelvic implant chosen by the surgeon can be used to display a position of the new acetabular center of rotation in comparison to the digitized acetabular center of rotation (Step 112). For instance, the distance between the centers of rotation can be displayed numerically (e.g., in mm) as a function of the acetabular coordinate system digitized in previous Step 106. Also, the anteversion and inclination of the actuation axis of the reamer, both as a function of the acetabular coordinate system, can be given numerically (e.g., in degrees) to guide the surgeon in the reaming. More precisely, the anteversion is calculated as the angle between the axis of the reamer and the pelvic frontal plane, and the inclination is the angle between the reamer axis projected onto the acetabular frontal plane and a cranial-caudal axis (Step 106).

Step 116 consists in the insertion of the pelvic implant in the acetabulum 11, but it is pointed out that this step can also be performed once the femoral head implant has been secured to the femur, according to the preference of the operator. A tracked impactor is preferably used. As the pelvic implant size is known, the diameter thereof and the known relation between the impactor and the pelvic implant is used with the tracking of the impactor to give the anteversion and the inclination of the pelvic implant. Also, the distances between the current and the digitized centers of rotation can be displayed. Therefore, the surgeon is guided during the use of the impactor so as to position the pelvic implant to a given position of the center of rotation thereof, and to a given orientation [with respect to anteversion and inclination] to provide a maximal range of motion and stability of the leg.

Although the pelvic implant is secured at this point to the pelvis 10, it is possible to adjust the position and orientation of the pelvic implant. Firstly, the tracked impactor, handle or like tool may be reconnected to the pelvic implant to serve as a lever in manipulating the pelvic implant with the tracked impactor, allowing position and orientation information (e.g., anteversion and inclination) to be calculated from the tracking of the impactor. Alternatively, points on the circular edge of the pelvic implant may be digitized to define a plane, with the normal to this plane being used to calculate the anteversion and the inclination, as suggested previously to obtain this information for the acetabulum.

Information typically provided with the use of the impactor includes: Display of generic 2D images, mosaic or mesh in 3D viewers along with impactor/cup assembly in real time and/or display targeting views to help the user to align with target values, frontal and lateral views, navigation of the impactor and cup, display of inclination, inclination adjusted with the pelvic tilt, anteversion, anteversion adjusted with the pelvic tilt angles in real time, display of the 3D position of the cup center of rotation relatively to the acetabulum center of rotation.

In Step 118, a bone model is digitized for the femoral head 21 and neck 22. The surface digitizing tool 150 is preferably used to create a 3-dimensional model of the femoral head 21 and neck 22. In this embodiment, it is preferred to simply cover the femoral head 21 and neck 22 with the flexible film 152.

As tracking references have been secured to the femur 20 and the pelvis 10 in Step 104, the points on the surface of the femoral head 21 are known as a function of the tracking of the respective tracking reference of the femur 20. As will be described hereinafter, a digital model of the femoral head and neck is produced, and may be displayed visually by the hip resurfacing CAS system.

It is pointed out that the neck/head connection is preferably identified in the digital model of the femoral head and neck. Information preferably obtained includes the lateral aspect of femur at the greater trochanter and the following 10 cm distally (as far as possible), internal aspect of femur at the lesser trochanter and the following distal region, and femoral neck itself (varus/valgus, anteversion). The head-neck junction is digitized or computed based on the points taken. If points are acquired automatically, collection of points can be taken by painting the femur. If points are acquired to build a mesh, points are taken on all the surface of the femur and not only on the frontal and transverse plane. The mesh can be constructed while points are acquired so users may take more points to have a more precise reconstruction.

The center of rotation of the femoral head may also be calculated from the digital model, for instance using a sphere fitter algorithm. If the center of rotation of the acetabulum is known, it may not be necessary to digitize the center of rotation of the femoral head.

In Step 120, the desired guide orientation is determined. More specifically, the resurfacing of the femoral head will be dependent on the orientation of a guide wire. Therefore, computer assistance is provided to the operator so as to orient the guide wire in view of the subsequent resurfacing of the femoral head.

Figure 5:
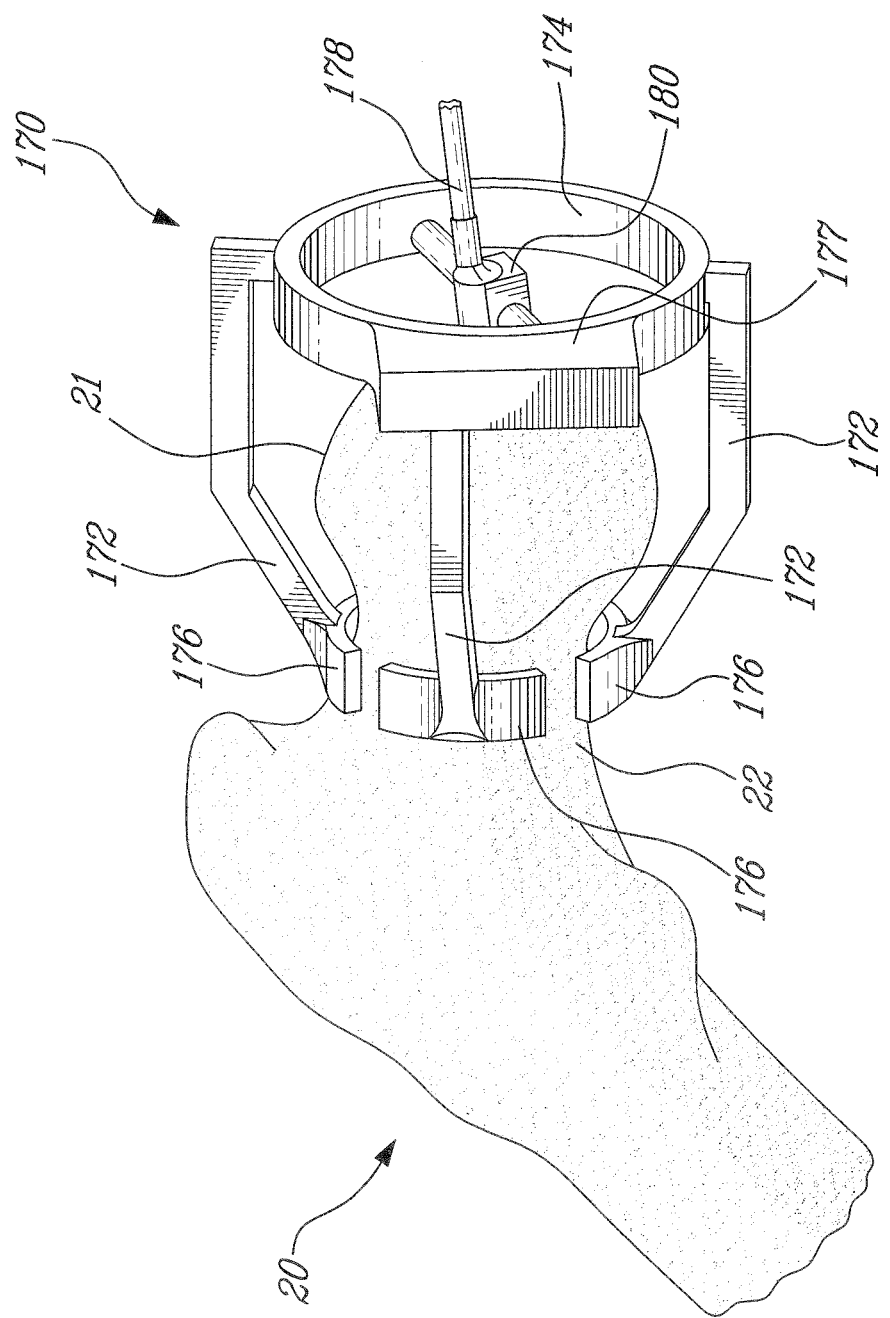
FIG. 5 is a perspective view of a positioning frame mounted to a femur in accordance with another preferred embodiment of the present invention.

Referring to FIG. 5, a drill guide positioning frame is generally illustrated at 170. The drill guide positioning frame 170 is provided to facilitate the planning of the desired guide orientation, and to guide the drilling operation.

The drill guide positioning frame 170 has legs 172 supporting an annular support 174. The three legs 172 illustrated in FIG. 5 are displaceable and securable to the annular support 174, so as to hold the support 174 fixed about the femoral head 21 in the manner illustrated in FIG. 5.

In the illustrated embodiment, the legs 172 each have an abutment end 176 that will contour a part of the femoral neck 22. The abutment ends 176 may be brought toward a common center by actuation of the lockable degrees-of-freedom (DOF) between the legs 172 and the annular support 174 so as to clamp onto the femoral neck 22. In a preferred embodiment, two translational DOFs are provided between the combination of the legs 172 and the support 174, such that the support 174 is displaceable in its plane. For instance, an actuator 177 is provided to actuate both translations DOFs.

In another embodiment, flexible film such as described in the surface digitizing tool 150 is provided on the abutments ends 176. In such a case, the flexible film is used to obtain the surface model of the femoral neck 22, at the surfaces of contact between the positioning frame 170 and the femoral neck 22. In such an embodiment, the position and orientation of the positioning frame 170 is tracked so as to relate the 3-dimensional surface data calculated from the flexible film to the frame of reference of the femur.

An alignment tube 178 is generally centrally positioned in the annular support 174. The alignment tube 178 is supported to the support 174 by a spherical joint 180, so as to be displaceable in two rotational DOFs. The two rotational DOFs are lockable, so as to set a desired orientation for the alignment tube 178. The alignment tube 178 is sized so as to accommodate a drill and like tools having an elongated stem. Therefore, the drill received in the alignment tube 178 is displaceable axially along the tube 178 so as to perform a drilling action.

In an embodiment, the support 174 is displaced in its plane by displacement with respect to the legs 172 so as to have the alignment tube 178 in a suitable approximate position with respect to where a guide hole must be drilled into the femoral head 21. The translational DOFs are then locked, in such a way that the only actuatable DOFs are the rotational DOFs of the spherical joint 180.

The drill or like registration tool is received in the alignment tube 178, and its longitudinal axis is tracked. Accordingly, the orientation of the drill is adjustable by the movement of the drill in the two rotational DOFs of the spherical joint 180. The support 174 may also be released from its locking relation with the legs 172 to adjust the position of the alignment tube 178 in the plane of the support 174.

Once a desired orientation of the alignment tube 178 is reached as obtained from the racking of the drill or like tool inserted in the alignment tube 178, the DOFs are locked whereby the drilling step may be performed.

It is pointed out that it is contemplated to motorize all or some of the DOFs of the drill guide positioning frame 170 to enable precise positioning of the alignment tube 178 with respect to the femoral head 21.

In order to plan the orientation of the guide wire, various views are provided such as the frontal and top views of the reconstructed femur. A template of the femoral implant over the femur model is also provided, as well as the following information: the initial CCD and anteversion angles, an initial template position, orientation and size with respect to the femoral center of rotation. The CCD is calculated as the angle between the projection of the guide wire on the femoral frontal plane and the longitudinal axis of the femur. Widgets are provided on screen to translate and rotate the template in each view. Selectors are provided to set the size of the implant and the neck diameter. If no flexible film is used in the positioning frame 170, the neck diameter is found by two moving lines parallel to the template axis on the digitized bone model. When the lines are on the contour of the neck, the diameter is determined. The CCD and anteversion angles are computed and displayed while the user is positioning the template. It is also contemplated to provide means to rotate the model so it can be viewed in 360 degrees. Implant position, orientation and size are computed and suggested to the operator as information to consider. Information that is preferably computed and displayed includes: the estimated range of motion, the estimated final leg length and offset, a graphical representation of the femoral preparation (final result). Potential dislocation and/or impingement is identified based on the cup position and orientation and the planned position and orientation of the femoral implant. If the femur is reconstructed with a mesh, the percentage of coverage may be provided. Indications of where notching may happen should also be provided.

In Step 122, the femur is altered for the insertion of the guide wire, using the positioning frame 170 as described previously (FIG. 3). In order to guide the operator in positioning and orienting the guide wire as planned, various information is provided, such as: generic 2D images, mosaic or mesh in 3D viewers along with guide wire/drill guide in real time and/or display targeting views to help the user to align with planned values, frontal and top views of the reconstructed femur, navigation of the guide wire with a drill guide, the CCD and anteversion angles, alignment views of the guide wire tracked with the drill guide on the CCD and anteversion axis found during the planning phase (aligning "bull's-eyes" or axes), the CCD and anteversion angles of the guide wire, audio and/or visual cues to let the operator know he/she is "in range" near the targeted angles by the means, the depth of the guide wire so the operator will be able to determine when the tip of the guide wire is near the lateral cortex of the proximal femur, potential notching with audio and/or visual feedback, and where this notching could potentially occur.

The same information can be provided for the insertion of a cannulated drill guide, with a display of the depth of drilling so the user will be able to determine when to stop drilling according to the chosen implant size.

Haptic devices can be used to ensure that the drilling only occurs when the orientation of the guide wire is as planned.

In Step 124, the femoral head 21 is resurfaced, by way of a reamer. It is contemplated to provide visual information to the operator at this step. However, the guides inserted in the femur ensure that the reaming follows planning. It is preferred that the operator keeps inspecting the actual femur especially during the cylindrical reaming, so as to avoid notching of the femoral neck 22. Information that can be provided is as follows: Tracking for position and orientation of the cylindrical reamer, generic 2D images, mosaic or mesh in 3D viewers along with cylindrical reamer in real time, frontal and top views of the reconstructed femur, navigation of the cylindrical reamer to track the reamed depth, orientation and position, the CCD and anteversion angles, a graphical representation of the result of the reaming, a pre-notching warning system based on probability to notch the cortex when the instrument is close to it.

For the planar reaming, information that can be provided is as follows: generic 2D images, mosaic or mesh in 3D viewers along with planar reamer in real time, frontal and top views of the reconstructed femur, tracking of the planar reamer to track the reamed depth, orientation and position, the CCD and anteversion angles, the distance between the head-neck junction and the plane surface of the planar reamer, indications to the operator to stop reaming based on the selected implant size, how much bone has been removed, the leg length and the offset based on the position of the planar reamer, a graphical representation of the result of the reaming, pre-notching warning system based on probability to notch the cortex when the instrument is close to it.

In Step 126, the femoral implant is secured to the resurfaced femoral head. Information that can be provided is as follows: position and orientation of the femoral component, generic 2D images, mosaic or mesh in 3D viewers, frontal and top views of the reconstructed femur, navigation of the cement mantel to track the position and the orientation of the implant, the distance between the implant and the plane surface of the femur, the leg length and the offset. It is contemplated to provide the possibility to attach the femoral implant while in place.

Although not illustrated in the method, there is provided the possibility to ream again the acetabulum after the placement of the femoral component if the initial reaming is not adequate, following the options provided in Step 114. Also, Step 116 could be performed at this point. Information that can be provided includes: the leg length and the offset based on the position of the reamer relatively to the acetabulum center of rotation and the position and orientation of the femoral implant with respect to the femur.

In the event that the acetabular cup is implanted at this point, the information that can be provided is as follows: tracking of the cup impactor, generic 2D images, mosaic or mesh in 3D viewers along with impactor/cup assembly in real time and/or display targeting views to help the user to align with target values, frontal and lateral views, display inclination, inclination adjusted with the pelvic tilt, anteversion, anteversion adjusted with the pelvic tilt angles in real time, 3D position of the cup center of rotation relatively to the acetabulum center of rotation, the leg length and the offset based on the position of the impactor relatively to the acetabulum center of rotation and location of the femoral component on the femur.

In Step 128, an analysis of range of motion is performed. Information is calculated, such as the range of motion of the joint after reduction, inclination, rotation and flexion/extension, possible dislocation (i.e., detect if the center of rotation has moved) and/or impingement.

Figure 4:
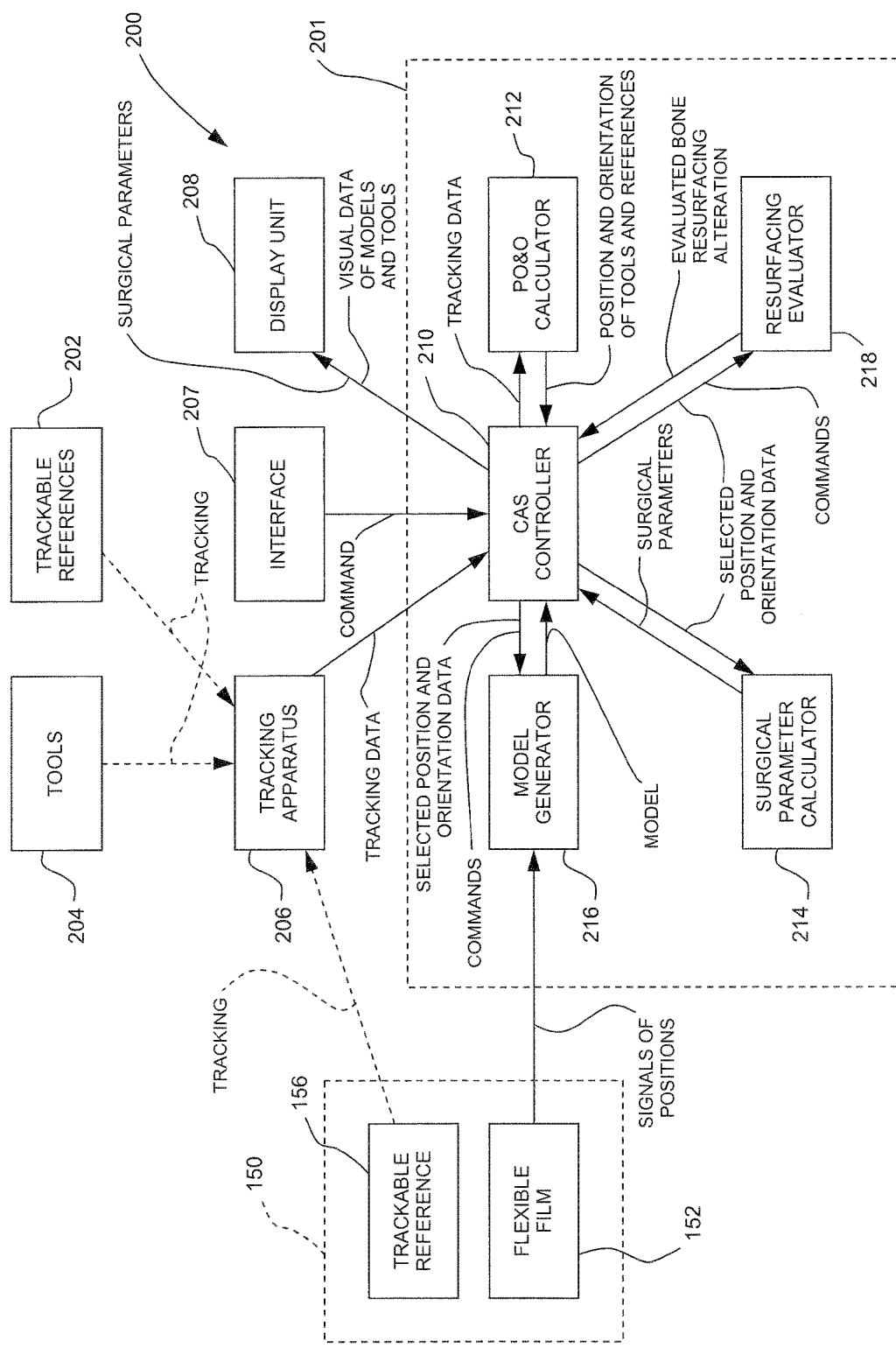
FIG. 4 is a block diagram of a hip resurfacing CAS system having a model generating system in accordance with another preferred embodiment of the present invention.

Referring to FIG. 4, a hip resurfacing CAS system is generally shown at 200. The CAS system 200 has a resurfacing processing unit 201. The resurfacing processing unit 201 is typically a computer or like device having a processor.

Peripherals are provided in association with the resurfacing processing unit 201. In view of the trackable references 202 that will be secured to the femur and pelvis to define frames of reference (Steps 104 and 106) and to the tracked tools 204 used throughout the method 100, tracking apparatus 206 is connected to the processing unit 201. The tracking apparatus 206 is provided to track the trackable references 202 and the tools 204 in the selected surgical environment. The tracking apparatus 206 may be any of optical sensors, RF sensors, magnetic sensors and the like used in CAS systems.

Interface 207 is connected to the processing unit 201. The interface 207 enables data entry and communications from the operator/surgeon of the system 200 to the processing unit 201. For instance, the interface 207 may be a keyboard, mouse and/or touch screen or the like.

A display unit 208 is connected to the processing unit 201. The display unit 208 provides information to the operator/surgeon throughout the steps of the method 100. The data may be in the form of numerical values, as well as virtual representations of bone models along with simulations of tools. Further detail about the data displayed by the display unit 208 will be given hereinafter.

The resurfacing processing unit 201 has a CAS controller 210. The CAS controller 210 is connected to the tracking apparatus 206 and to the interface 207, so as to receive information therefrom. More specifically, the CAS controller 210 receives tracking data from the tracking apparatus 206, which tracking data will be interpreted by the processing unit 201. The CAS controller 210 receives user commands given by the operator of the system 200 using the interface 207, and essentially controls the flow of information between the peripherals 206 to 208, and between the other components 212, 214, 216, and 218 of the resurfacing processing unit 201. The CAS controller 210 performs certain tasks as well, such as calibration of tools.

The CAS controller 210 is also connected to the display unit 208. The CAS controller 210 provides display data, in the form of numerical values and visual representations, to the display unit 208. The display unit 208 displays this information.

A position/orientation calculator 212 is connected to the CAS controller 210. The position/orientation calculator 212 receives the tracking data of the tracking apparatus 206 from the CAS controller 210. The information provided to the CAS controller 210 by the position/orientation calculator 212 is in the form of the position/orientation of a selected item of the trackable references 202 or tools 204. For instance, following the method 100, the data provided by the calculator 212 may be the pelvic and femoral coordinate systems from the trackable references 202. As another example, the data takes the form of a real-time orientation of the operating axis of one of the tools 204, such as the axis of a reamer, or a real-time position of a tip of one of the tools 204, such as a registration pointer.

A center calculator 214 (i.e., a surgical parameter calculator 214) is associated with the CAS controller 210. The center calculator 214 is provided to digitize the center of rotation of the pelvis (as described for Step 112) and the center of rotation of the femoral head (optionally in Step 118). The center calculation is performed using the position/orientation data calculated by the position/orientation calculator 212, as well as commands from the CAS controller 210.

In the embodiment of FIG. 3, the center calculation is performed using the surface digitizing tool 150 and/or the positioning frame 170 which provide meshes of points representing the surface of the acetabulum (Step 112), of the femoral head and neck (Step 118), and of the femoral neck (Step 122). An indication that the center calculation is to be performed by the center calculator 214 is commanded by the CAS controller 210, for instance as a response to a command from the operator using the interface 207. The position of the centers is therefore calculated with respect to the coordinate systems (Step 106), and the information is updated in real-time by the CAS controller 210.

A model generator 216 is associated with the CAS controller 210 and with the position and orientation calculator 212 in a model generator system. The model generator 216 receives the signals representing the meshes of points from the flexible film (of the tool 150 or the frame 170) in combination with commands from the CAS controller 210, following Steps 112, 118 and 122. The model generator creates 3-dimensional models from these signals, and combines the model to the position and orientation of the trackable member 156 to relate the bone model to the frames or reference. For instance, in Step 118, a surface model of the femoral head and neck is obtained. The surface model is associated with the coordinate systems obtained from the tracking of the trackable references 202.

More specifically, the model generator 216 obtains a signal from each of the micro-sensor elements when the film is shaped to model the femoral head and neck and/or the acetabulum. The signals are used, along with the individual position of each of the micro-sensor element, to determine a shape variation of the film at each of the micro-sensor element. Subsequently, the 3D model of the bone element (i.e., femoral head/neck, acetabulum) is generated from the shape variation and the individual position of each of the micro-sensor elements.

A resurfacing evaluator 218 is provided in association with the CAS controller 210. The resurfacing evaluator 218 (is provided to determine the evaluated bone resurfacing alteration, which is the effect of a resurfacing tool (from the tools 204) on the bone model. Accordingly, bone model data is provided by the model generator 216, along with the position and orientation of a reaming tool as determined by the CAS controller 210 from tool geometry data and an orientation of a bone-altering tool (such as a drill) from the tools 204.

In the case of femoral head resurfacing, as the precision of the reaming must be respected, it has been described previously that a guide wire is provided, in order to drill a guiding bore in the femoral head prior to reaming. Therefore, the evaluated bone resurfacing alteration is indicated as a function of the orientation of the axis of the drill guide. Therefore, information associated with a potential wrongful reaming is provided to the operator, such that the operator is guided into drilling the drill guide in a suitable orientation in view of the effects on resurfacing. The resurfacing evaluator 218 may also be used to calculate the effect of acetabulum reaming on associated data (pelvic center of rotation, anteversion, etc.)

Throughout surgery, the display unit 208 provides the data discussed above. For instance, the output of the model generator 210 is converted by the CAS controller 210 to a virtual model of the bone surface to be altered, for instance with virtual real-time representations of the tools with respect to the bone models. Accordingly, warning can be signaled to the operator/surgeon if the effects of resurfacing are outside acceptable standards. Again, in femoral head resurfacing, the femoral neck must not be nicked, whereby drill guide axis data can be associated with a warning signal to guide the operator/surgeon in adjusting the orientation of the drill.

Moreover, numerical information is also provided to the operator, which numerical information is described previously for the steps of the method 100.

Various instruments can be used, such as blunt tracked pointers (straight or curved), adapted to fit on a rotational tracker or a universal handle to paint bones (acetabulum, femur, etc.). The drill guide or guides can be designed to fit on a universal handle or a rotational tracker. A mechanism may be used to block/hold the position and the orientation of the drill guide. Planar reamer is modified to be used in conjunction with the rotational tracker. Technology to have appropriate drilling instrument if the user wants to navigate the drill bit only.

In other contemplated options there are the possibility to navigate the guide wire, the guide wire and the cannulated drill bit or only the drill bit, the possibility to rotate, translate and zoom the viewers, the animation or illustration to describe to the operator the upcoming tasks, the possibility to take snapshots, menus allowing selection of options and parameters during the procedure, allowing navigating through the surgical steps in the application, step-driven (wizardlike sequence of pages), status icons to display tracking state of an instrument, volume view/aim camera to display in space the location of the trackers seen by the camera, give information on the tracked state of a tracker (out of volume, missing sphere, IR interference, etc).

The invention claimed is:
1. A system comprising
   a drilling tool;
   a positioning frame for aligning a position and orientation of the drilling tool with respect to a bone element, the positioning frame including a connector portion comprising legs displaceable relative to one another so as to be configured to releasably grasp the bone element between free ends of the legs;

a support portion operatively connected to the connector portion and positionable with respect to a portion of the bone element to be drilled, an alignment tube operatively connected to the support portion, the alignment tube being adapted to receive an end of the drilling tool to align the drilling tool with the bone element; and motorized joints between the alignment tube and the support portion to adjust an orientation of the alignment tube with respect to the bone element, as a function of a grasping of the bone element by the free ends of the legs, and between the legs and the support portion, whereby the motorized joints cooperatively allow movement of the alignment tube relative to the connector portion for the drilling tool to be displaceable with respect to the bone element to be drilled, the motorized joints between the alignment tube and the support portion providing at least two rotational degrees of freedom of orientation adjustment to the alignment tube relative to the bone element.

2. The system according to claim 1, wherein the motorized joints between the connector portion and the support portion to adjust a position and orientation of the alignment tube are lockable.

3. The system according to claim 1, wherein the motorized joints between the support portion and the alignment tube are lockable.

4. The system according to claim 1, wherein the free ends of the connector portion grasping the bone element each have a film of micro-sensor elements, with each micro-sensor element related in a network affected by a shape of the film, the film being flexible to conform to a shape of the bone element so as to provide data pertaining to a geometry of the bone element.

5. The system according to claim 1, wherein the bone element is a femur, and the connector portion is configured to releasably grasp a femoral neck of the femur, and the alignment tube is aligned with a femoral head of the femur.

6. The system according to claim 1, wherein the support portion has an annular body, with the alignment tube being held generally in a center of the annular body, and wherein the connector portion has three of said legs projecting from the annular body.

* * * * *